United States Patent

Mortier

[11] Patent Number: 5,810,822
[45] Date of Patent: Sep. 22, 1998

[54] APPARATUS FOR CORRECTING LONG BONE DEFORMATION

[76] Inventor: Jean-Pierre Mortier, 71 rue Claude Bernard, 75005 Paris, France

[21] Appl. No.: 732,318
[22] PCT Filed: Apr. 26, 1995
[86] PCT No.: PCT/FR95/00544
  § 371 Date: Oct. 21, 1996
  § 102(e) Date: Oct. 21, 1996
[87] PCT Pub. No.: WO95/28887
  PCT Pub. Date: Nov. 2, 1995

[30] Foreign Application Priority Data

Apr. 27, 1994 [FR] France .................................. 94 05332

[51] Int. Cl.⁶ .................................................. A61B 17/80
[52] U.S. Cl. ............................... 606/69; 606/75; 606/101
[58] Field of Search .................................. 606/75, 72, 69, 606/70, 71, 73, 67, 60, 96, 98, 101, 82, 88

[56] References Cited

U.S. PATENT DOCUMENTS

| | | | |
|---|---|---|---|
| 2,494,229 | 1/1950 | Collison | 606/96 |
| 4,632,102 | 12/1986 | Comparetto | 606/82 |
| 4,788,970 | 12/1988 | Kara et al. | 606/96 |
| 4,848,328 | 7/1989 | Laboureau et al. | 606/75 |
| 4,913,144 | 4/1990 | Del Medico | 606/75 |
| 5,197,966 | 3/1993 | Sommerkamp . | |
| 5,470,335 | 11/1995 | Du Toit | 606/73 |
| 5,591,168 | 1/1997 | Judet et al. | 606/65 |

FOREIGN PATENT DOCUMENTS

| | | |
|---|---|---|
| 0 552 109 | 7/1993 | European Pat. Off. . |
| 2362616 | 3/1978 | France . |
| 2456506 | 12/1980 | France . |
| 2676353 | 11/1992 | France . |
| 2686012 | 7/1993 | France . |
| 3724479 | 2/1989 | Germany . |
| 2126903 | 4/1984 | United Kingdom . |
| 94/02073 | 2/1994 | WIPO . |

*Primary Examiner*—Guy V. Tucker
*Attorney, Agent, or Firm*—William H. Eilberg

[57] ABSTRACT

The apparatus of the invention includes at least a first device (21) with a rigid elongated body (1) including two main sections angularly coupled with each other by an angular coupling region forming an angle substantially equal to the angular correction to be applied to a bone (18). First anchoring elements (5) shaped as pins are provided to be transversely attached to the proximal portion (24) of the bone (18); second anchoring elements in the form of bone screws (26) are provided to be attached to the diaphysis portion of the bone (18). The first device (21) is positioned on the bone (18) following an opening osteotomy (23). A second device (22) n the form of a four pin clip, may be positioned on an adjacent bone (19) on each side of a closure osteotomy (27) in order to complete the correction. A Hallux Valgus can thus be corrected.

14 Claims, 8 Drawing Sheets

APPARATUS FOR CORRECTING LONG BONE DEFORMATION

BACKGROUND OF THE INVENTION

This application is filed under 35 U.S.C.371, based on PCT/FR95/00544 which was filed on Apr. 26, 1995.

The present invention concerns equipment for correcting deformation of certain long bones, inparticular small long bones in the human body. The equipment of the invention is used in particular tocorrect deformation, mainly hallux valgus deformation, of the hallux (innermost digit) of the foot.

The hallux comprises three long bones in succession articulated to each other, namely the first metatarsal, the first phalange and the second phalange. A hallux valgus deformation is an excessive inward deviation of the hallux.

It is tempting to correct this excessive inward deviation by removal of bone from the first metatarsal (interior opening or exterior closing osteotomy). Unfortunately, until now, precise angular correction has not been possible for want of suitable osteosynthesis equipment.

Document WO-A-94 02073 describes an osteosynthesis clip for the head of the tibia or the head of the femur. This device has a rigid body, which is a priori non-deformable, curved (S-shape) and fastened at both ends to two divergent pins with teeth causing compression of bone fragments on either side of the fracture. Apart from the fact that a device of this kind is not capable of penetration into the cortical bone, which penetration is necessary for correcting deformations of the feet, and does not have any angular modification action due to its shape, any correction achieved is independent of the shape of the rigid body and depends only on the angle of the osteotomy prior to insertion of the pins. Given that it is always difficult to achieve a precise angle in osteotomy, the device does not easily achieve a precise angular correction. Also, the device compresses the bone fragments which means that it is not suitable for interior opening osteotomy.

Document FR-A-2 686 012 describes a plate and blade device for angular correction of the tibia. Because of the S-shape of the body and because of the presence of a blade member, the device is suitable only for correction of the tibia and is not appropriate for other bones such as the long bones of the foot. Also, because the body has to be very rigid to withstand the high mechanical stresses on the tibia, it is not deformable and the angle between the blade member and the body is fixed. The angular correction obtained by osteotomy is therefore adjusted by varying the angle at which the blade member penetrates the epiphysis, and by bringing the diaphysis progressively into contact with the body. This adjustment is difficult and delicate. Also, an offset results between the body and the external surface of the epiphysis, depending on the angular correction made. The device is not suitable for treatment of small long bones as the distance between the penetration orifice of the blade member and the osteotomy is then too small to allow variation in the angle of penetration. If an acute penetration angle were chosen, the blade member would impinge on the osteotomy.

Document EP-A-0 552 109 describes a clip for pinning a ligament to a bone. A device of this kind is not capable of angular correction and the proximity of its pins and its locking fingers means that it is unable to support an osteotomy.

Document FR-A-2 362 616 describes a clip to be shaped into a tube to hold a bone straight. This device is not capable of angular correction.

The problem to which the present invention is addressed is therefore that of providing equipment for easy and effective correction of deformation of small long bones, in particular hallux valgus deformation of the hallux. The equipment must provide the precise angular correction of itself, without requiring great accuracy of the osteotomy. The equipment must hold the adjacent portions of the bone at the correct angle after osteotomy, without making the bone fragile, and in particular allowing a maximum distance between the osteotomy and the fixing members penetrating the bone.

The equipment of the invention must also be usable for correcting associated or non-associated deformations in the vertical plane, such as lowering or elevation of the metatarsal, or in rotation (supination or pronation), or lengthwise (shortening or extension). It must also be usable for correction of other metatarsals, especially problems with rotation of the fifth metatarsal, and for correction of other small long bones such as the bones of the hand.

SUMMARY OF THE INVENTION

To achieve these and other objects the equipment of the invention for correcting deformation of long bones includes at least one bone holding device including:

a rigid elongate body having two rectilinear main segments joined together by an angled joining area at an angle (A) to each other which can be varied so that it is substantially equal to the required angular correction, said body being made from a material and having a shape adapted to withstand without breaking and to retain permanent angular deformation in the angled joining area, first anchor means on the first main segment of the body adapted to be fixed transversely into the bone in a direction at a particular angle (B) such as right angle to the longitudinal axis of the bone, the first anchor means including at least one pin extending in a direction substantially at said particular angle (B) to the longitudinal axis of the first main segment of the body, second anchor means on the second main segment of the body adapted to be fixed transversely in the bone at a subsequent stage, after fixing of the first anchor means so that after opening or closing osteotomy between two adjacent portions of the bone at an angle substantially equal to the required correction, and after anchoring of the first anchor means of the device at the particular angle (B) in the bone such that the angled joining area is in line with the osteotomy the device determines the angular offset between the two adjacent bone portions, subsequent anchoring of the second anchor means fixing the angular offset.

In a first embodiment of the invention:

the second anchor means include at least one hole adapted to fit a bone screw, the anchor means are adapted to penetrate the bone and project from the concave face of the body.

A device of this kind including two body main segment pins is a clip suitable for correcting deformation of the first metatarsal.

A device of this kind including a single body main segment pin is a clip suitable for correcting deformation of the fifth metatarsal.

The invention also provides a complementary device having a rigid elongate body comprising a rectilinear first main segment and a rectilinear second main segment joined together at an angled joining area and wherein:

first anchor means include a first pair of pins offset longitudinally on the body, second anchor means include a second pair of pins offset longitudinally on the body, the pins project from the convex side of the body.

This complementary device is a clip suitable for correcting deformation of the first metatarsal.

The combination of the two devices is suitable for correction of the first metatarsal and the first phalange.

Other objects, features and advantages of the present invention will emerge from the following description of specific embodiments of the invention given with reference to the appended drawings.

DETAILED DESCRIPTION OF THE INVENTION

Figure 3:
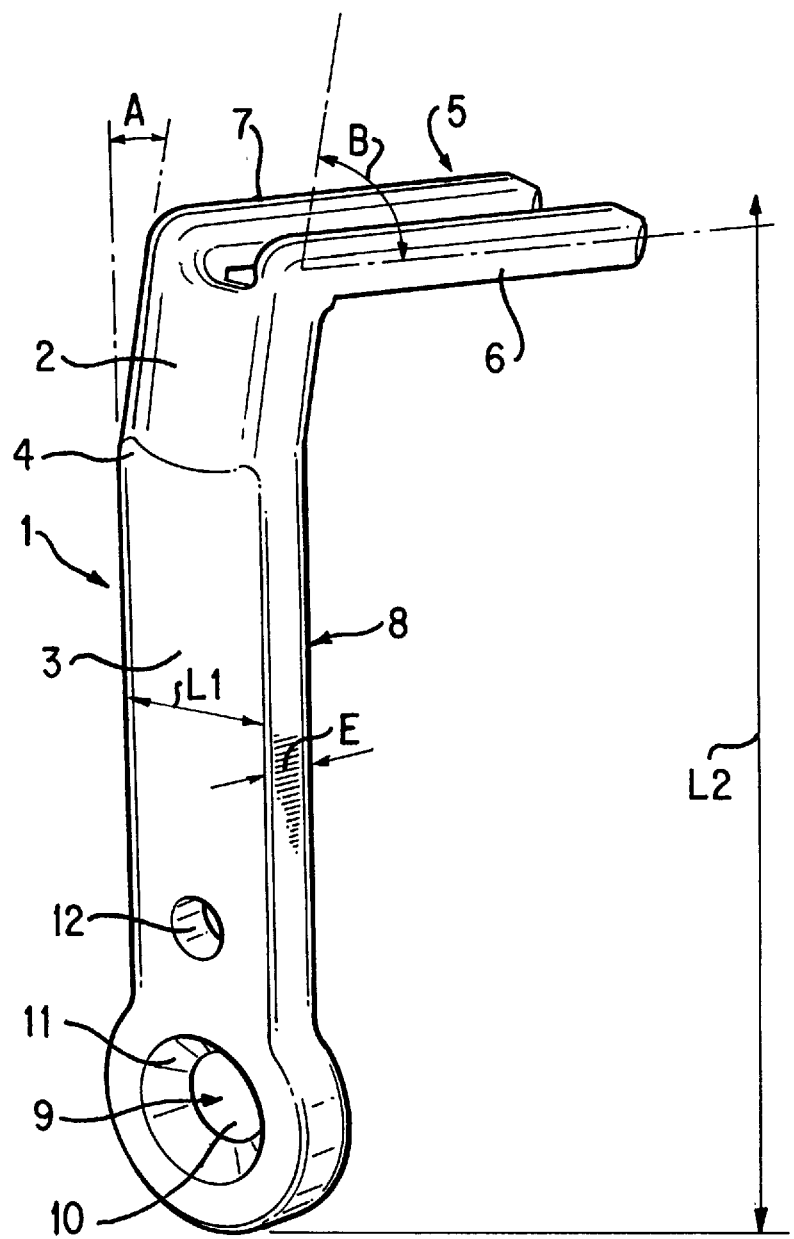
FIG. 3 is a perspective view of one embodiment of a device of the present invention.

In the embodiment of the invention shown in FIG. 3 the device of the invention includes a rigid elongate body 1 having a rectilinear first main segment 2 and a rectilinear second main segment 3 joined together by an angled joining area 4 at a chosen angle A to each other equal to the angular correction to be applied to a bone.

First anchor means 5 are provided on the first main segment 2 of the body 1 and are adapted to be fixed transversely in the bone. In the embodiment of the invention shown the first anchor means 5 comprise two parallel pins 6 and 7 attached to the body 1, parallel to each other and generally oriented at a particular angle B (such as a right angle) to the longitudinal direction of the first main segment 2 and projecting from the concave face 8 of the body 1. The two parallel pins 6 and 7 are offset laterally relative to each other and lie in a plane at the particular angle B (such as a right angle) to the longitudinal axis of the first main segment 2 of the body 1. The pins 6 and 7 can thus be fixed into the bone during a first fixing step.

Second anchor means 9 are provided on the second main segment 3 of the body 1 and are fixed transversely in the bone at a later stage, after fixing the first anchor means 5. In the embodiment of the invention shown in the figure the second anchor means 9 include a hole 10 into which fits the head of a screw whose shank projects from the concave face 8 of the body 1. The hole 10 has a spherical annular portion 11, for example, matching a spherical bearing surface on the head of a bone screw.

The body 1 may advantageously also include near the hole 10 receiving the bone screw a secondary hole 12 for a removable pin for fixing the device temporarily to the bone or for strengthening its permanent fixing.

The angle A can advantageously be equal to approximately 15°. However, this angle can be different depending on the correction required to the metatarsus verus.

In all embodiments of the invention there is advantageously provision for deforming the body 1 in the angled joining area 4 to modify the angle A to match it to the required vertical correction, if any, associated with a lateral correction. To this end the body 1 is made from a material able to withstand without breaking and to retain permanent angular deformation in its angled joining area 4. Biologically compatible stainless steel can be used. The body is also given a shape enabling permanent angular deformation: in the angled joining area 4 the body has a thickness E substantially less than its width L1.

In the embodiment of the invention shown in FIG. 3 the body 1 is in the form of an elongate plate the width L1 of which is substantially greater than the thickness E. Its length L2 is between one third and one half the length of the bone to be corrected. For an application to correct a first metatarsal the length L2 is advantageously between approximately 2 cm and approximately 3 cm.

Figure 4:
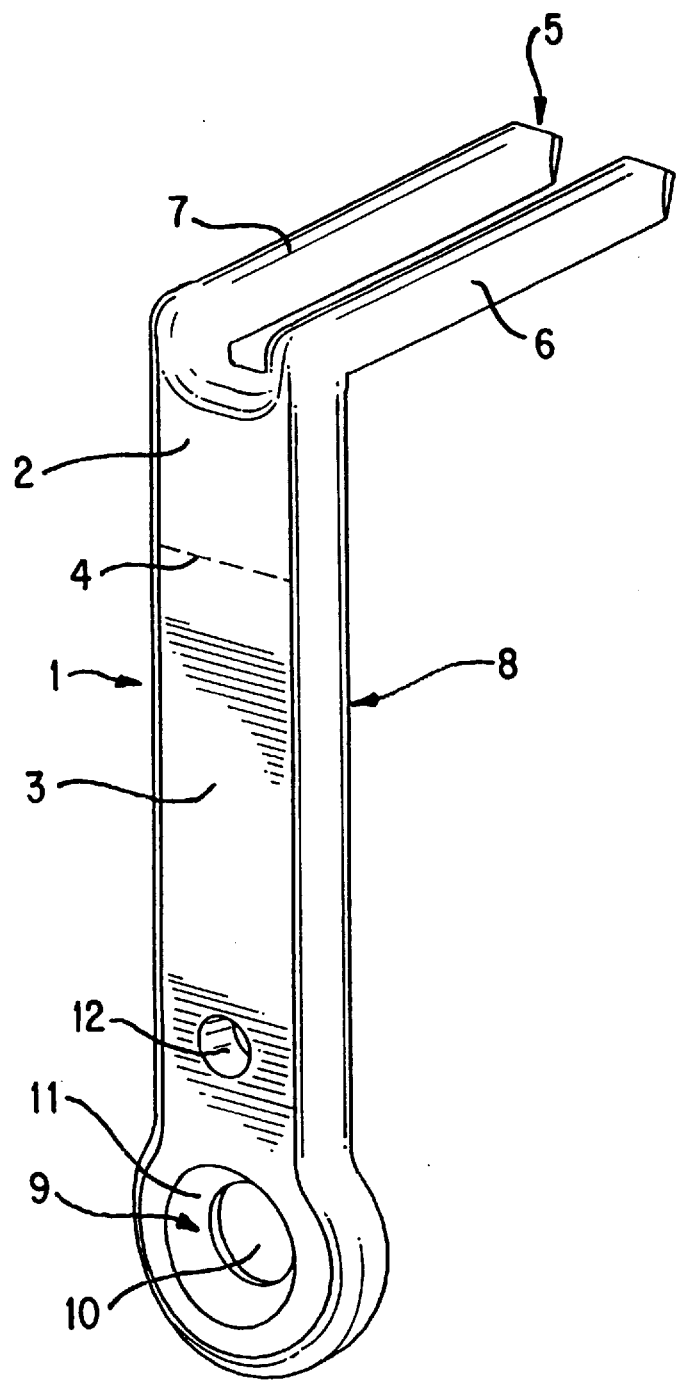
FIG. 4 is a perspective view of a variant of the device from FIG. 3.

In the variant shown in FIG. 4 the device includes the same components as the FIG. 3 embodiment of the invention and the common components are identified by the same reference numbers.

However, in this embodiment of the invention the body 1 is a rectilinear plate and its angled joining area 4 is bent to an appropriate angle using a bending device, according to the required angular correction of the bone.

Figure 5:
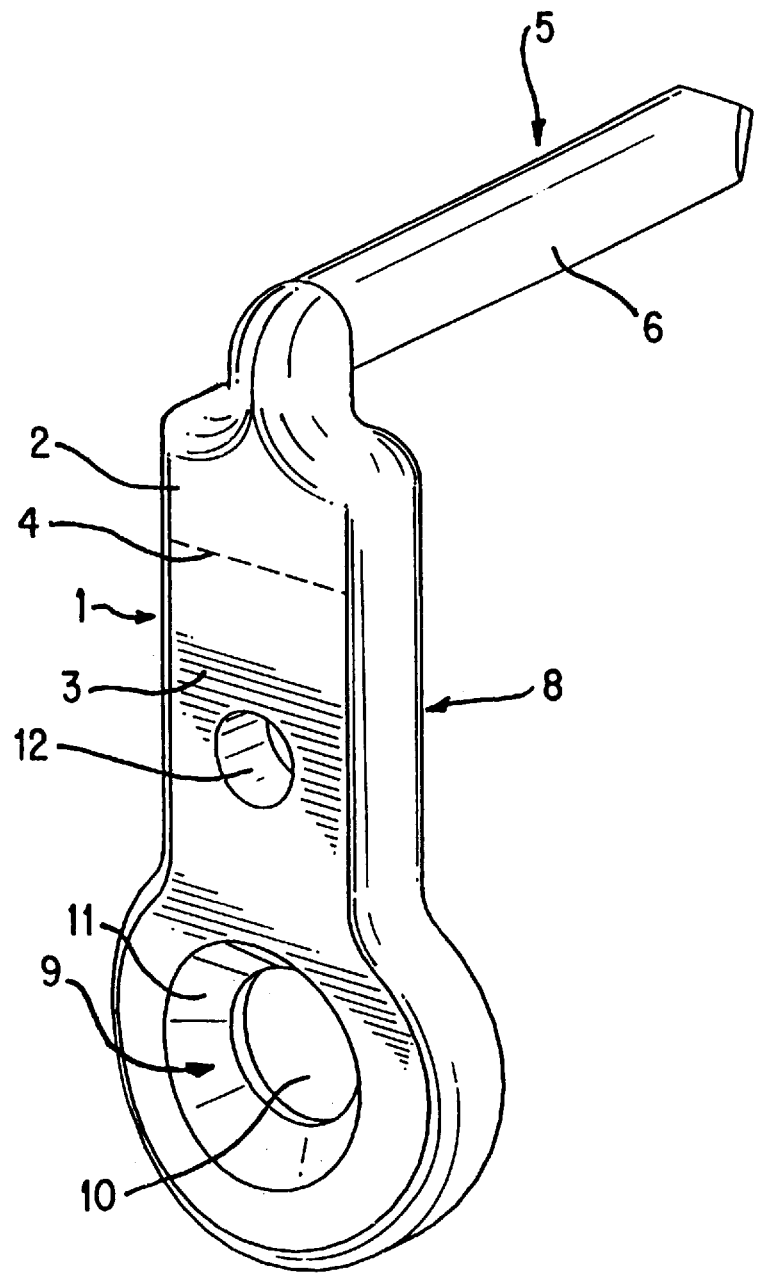
FIG. 5 is a perspective view of a second variant of the device from FIG. 3, suitable for correction of the fifth metatarsal.

In the variant shown in FIG. 5 the device includes similar components to those of the FIG. 3 embodiment of the invention and these similar components are identified by the same reference numbers.

In the FIG. 5 variant the body 1 is also a rectilinear plate and the angled joining area 4 is bent to an appropriate angle by means of a bending device.

Also, in this variant, the first anchor means 5 comprise a single pin 6. This device is suitable for correction of the fifth metatarsal.

The pin or pins of the first anchor means 5 are at a particular angle B to the first segment 2 of the body 1. The invention provides a drilling guide for boring penetration holes in the bone at the same angle B to the longitudinal direction of the bone.

Figure 7:
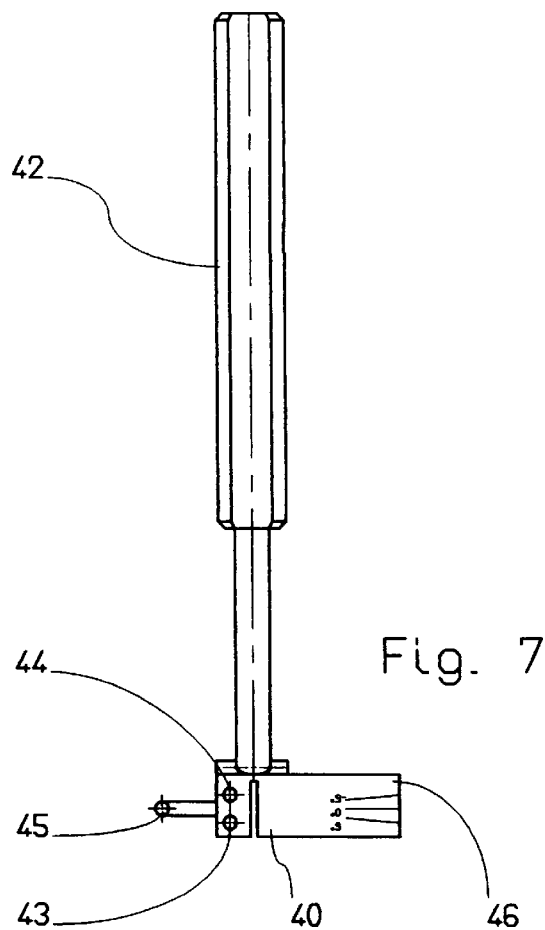
FIG. 7 is a top view of a drilling guide of the invention for boring tunnels in the bone for insertion of first anchor means.
Figure 8:
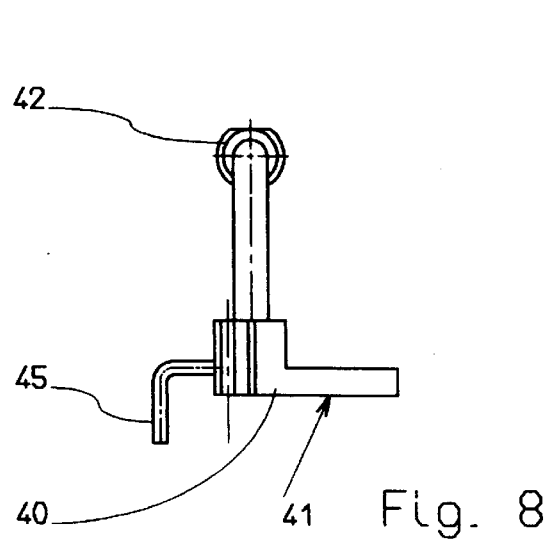
FIG. 8 is a side view of the drilling guide from FIG. 7.
Figure 9:
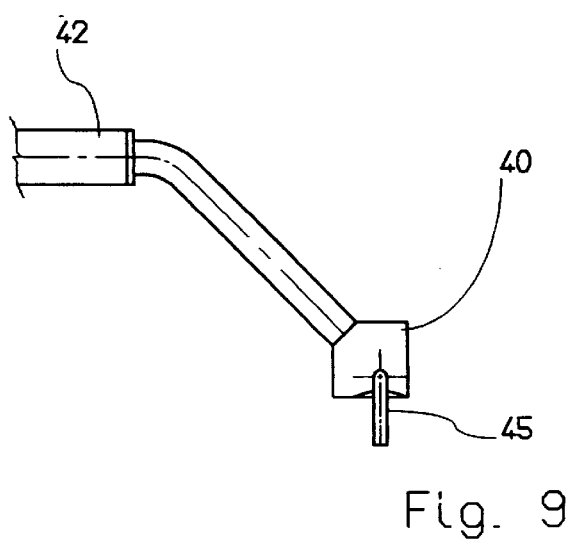
FIG. 9 is a front view of the drilling guide from FIG. 7.

The drilling guide used for this purpose is shown in FIGS. 7 through 9 and has a body 40 with a plane lower bearing face 41. It is held by a transverse handle 42 and has two through-holes 43 and 44 perpendicular to the lower bearing face 41. In this embodiment of the invention the angle B is a right angle. Alternatively, the holes 43 and 44 can be inclined to provide an angle B other than 90°. A longitudinal hook 45 locates the drilling guide relative to a bone end. Graduations 46 on the end of the body 40 allow lateral orientation adjustment of the bone parts on either side of an osteotomy if necessary.

Figure 10:
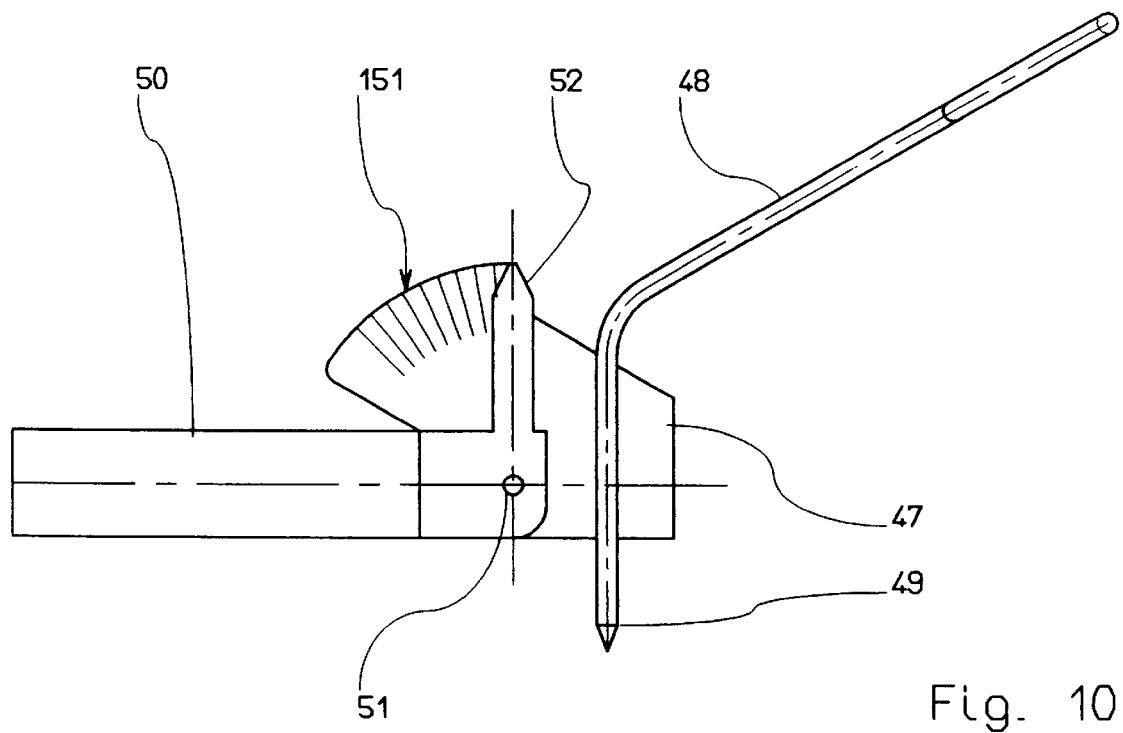
FIG. 10 is a side view of a protractor of the invention used during surgery to measure the angle of the required angular correction.
Figure 11:
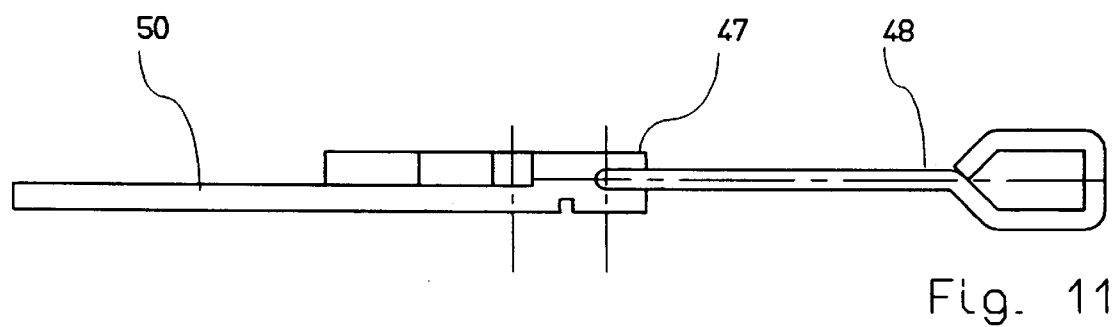
FIG. 11 is a top view of the protractor from FIG. 10.

To measure the required angle A of angular correction during surgery it is possible to use a protractor as shown in FIGS. 10 and 11. This device has a body 47 fastened to a handle 48 and including a rod 49 which is inserted into one of the tunnels previously bored in the bone using the drilling guide shown in FIGS. 7 through 9. A feeler 50 is articulated to the body 47 about a transverse axis 51. The body 47 is applied to the proximal part of the bone after osteotomy and the feeler 50 is applied to the distal part of the bone while adjusting the inclination of the distal part of the bone to obtain the required correction. The angle between the body 47 and the feeler 50 can then be read off graduations 151 on the body across which moves a pointer 52 on the feeler 50.

Figure 12:
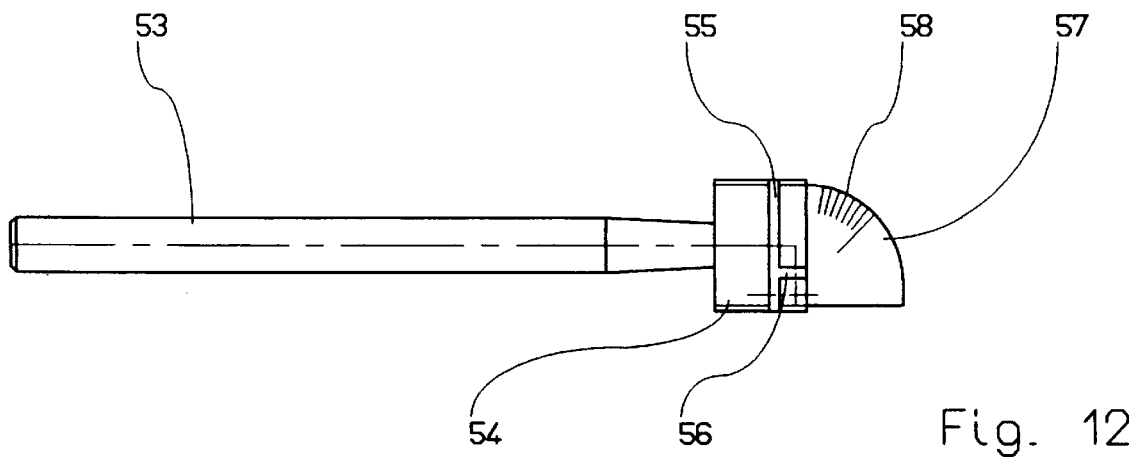
FIG. 12 is a side view of a first bending device member of the invention for imparting to the clip an angle conforming to the required angular correction.
Figure 13:
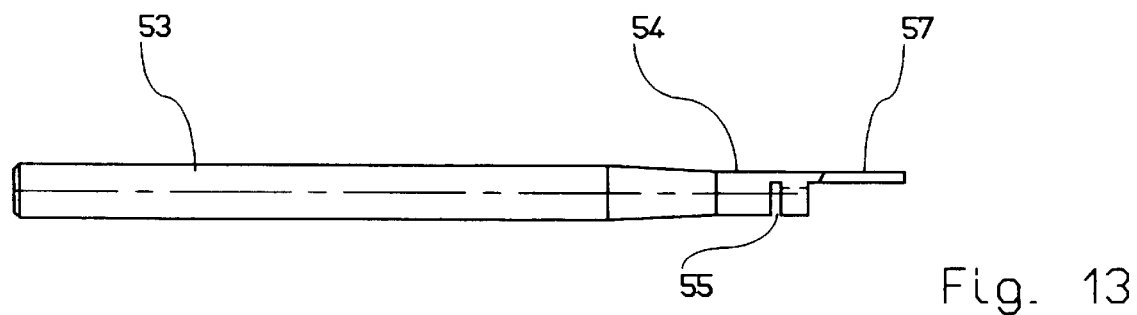
FIG. 13 is a top view of the first bending device member from FIG. 12.

A bending device is used to conform the body 1 to the required angle A. The bending device includes a first member shown in FIGS. 12 and 13 having a handle 53 and a body 54. The body 54 includes a wide transverse groove 55 and a narrow longitudinal groove 56 shaped to enable lateral insertion of the end of the clip including the pins of the first anchor means 5. The pins are inserted into the wide transverse groove 55. The end of the body 1 passes through the narrow longitudinal groove 56. A lateral flange 57 carrying angular graduations 58 is used to measure the angle A in the angled joining area of the body 1.

Figure 14:
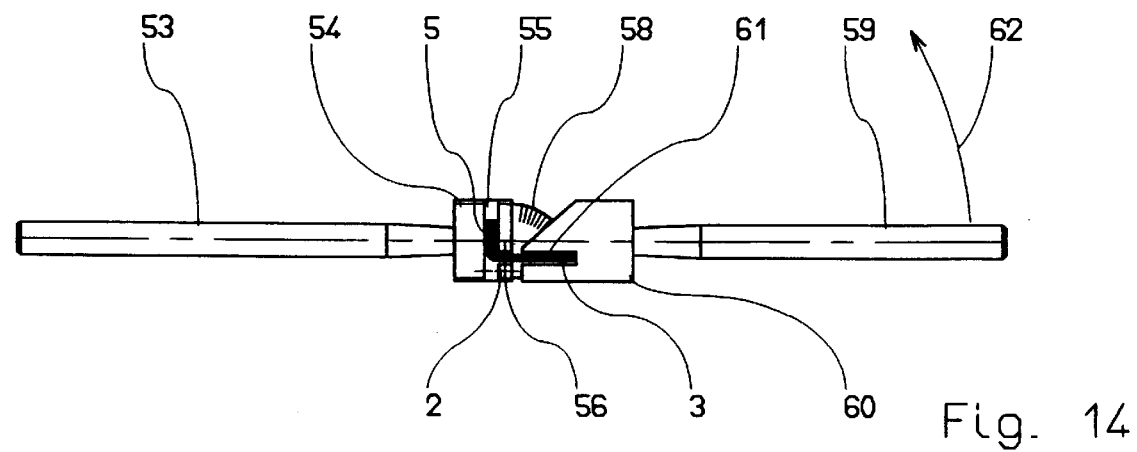
FIG. 14 is a side view of a second bending device member used in association with the first member from FIG. 12 to bend a clip to the required correction angle.

The angle A is adjusted using a second member shown in FIG. 14 including a handle 59 and a body 60 which has a longitudinal slot 61. The second main segment 3 of the body 1 is inserted longitudinally into the slot 61, opposite the first main segment 2 of the body 1 inserted into the first member shown in FIGS. 12 and 13. By maneuvering the handles 53 and 59 as shown by the arrow 62, the body 1 can be bent to the required angle A, read off on the graduations 58.

Figure 6:
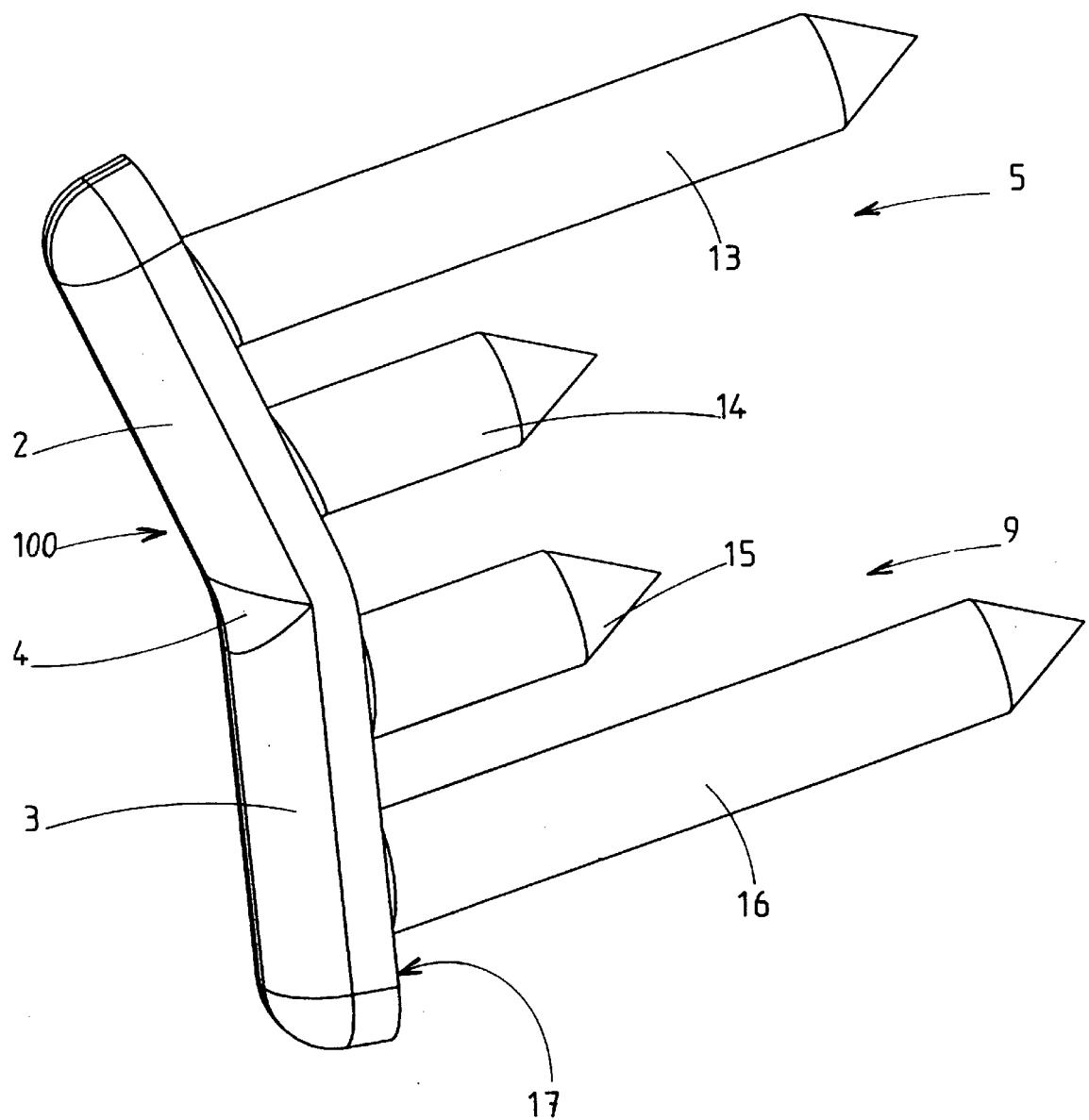
FIG. 6 is a perspective view of one embodiment of a complementary device of the invention.

FIG. 6 shows a complementary device of the invention having a rigid elongate body 100 comprising a rectilinear first main segment 2 and a rectilinear second main segment 3 joined together in an angled joining area 4 at an angle substantially equal to the angular correction required, for example equal to approximately 10°. The first main segment 2 includes first anchor means 5 and the second main segment 3 includes second anchor means 9.

In this complementary device, the first anchor means 5 include a first pair of pins 13 and 14 offset longitudinally on the body 100. The end pin 13 is longer than the intermediate pin 14.

Similarly, the second anchor means 9 include a second pair of pins 15 and 16 offset longitudinally on the body 100, the end pin 16 being longer than the intermediate pin 15.

The pins 13, 14, 15 and 16 are advantageously parallel to each other and project from the convex side 17 of the body 100.

The length of the body 100 is advantageously between one third and one half the length of the bone to be corrected. In the case of correcting the first phalange of the hallux, the length of the body 1 is advantageously between approximately 1 cm and approximately 2 cm.

Figure 2:
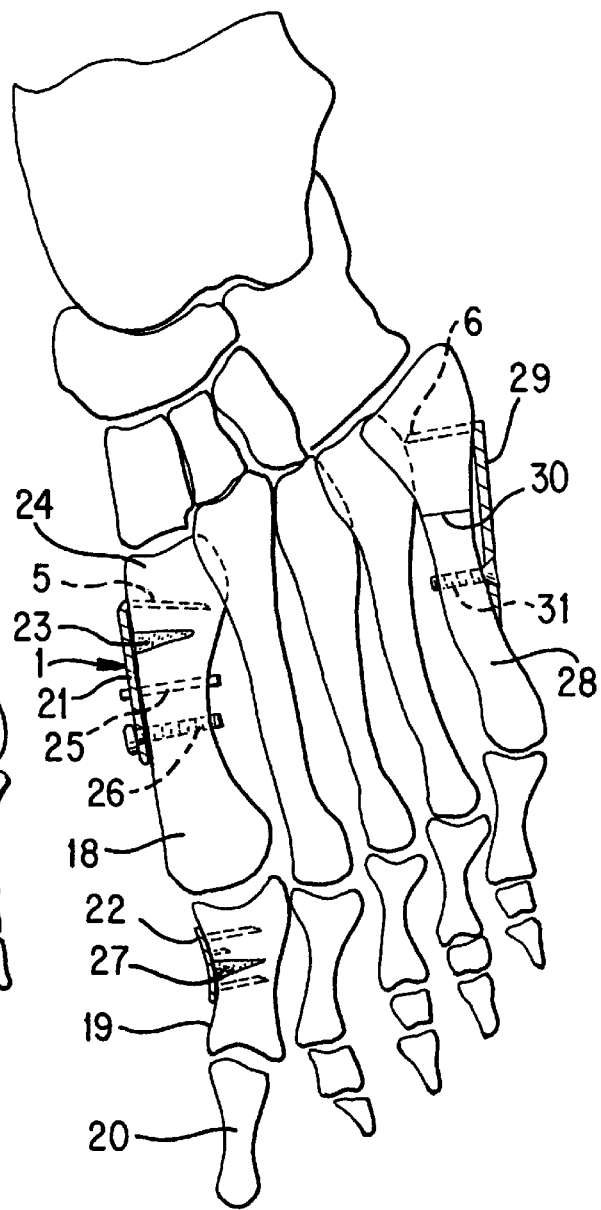
FIG. 2 is a top view of the bones of the foot from FIG. 1 after correction of the hallux using the equipment of the present invention; this figure also shows corrections of the fifth metatarsal.

As shown in FIG. 2, the equipment used to correct deformation of the foot, in particular hallux valgus deformation, advantageously includes a first device such as a clip 21 shown in FIGS. 3 to 5 shaped to fit to the first metatarsal 18 of the hallux and a complementary second device such as the clip shown in FIG. 6, shaped to fit to the first phalange 19 adjacent said first metatarsal 18.

Figure 1:
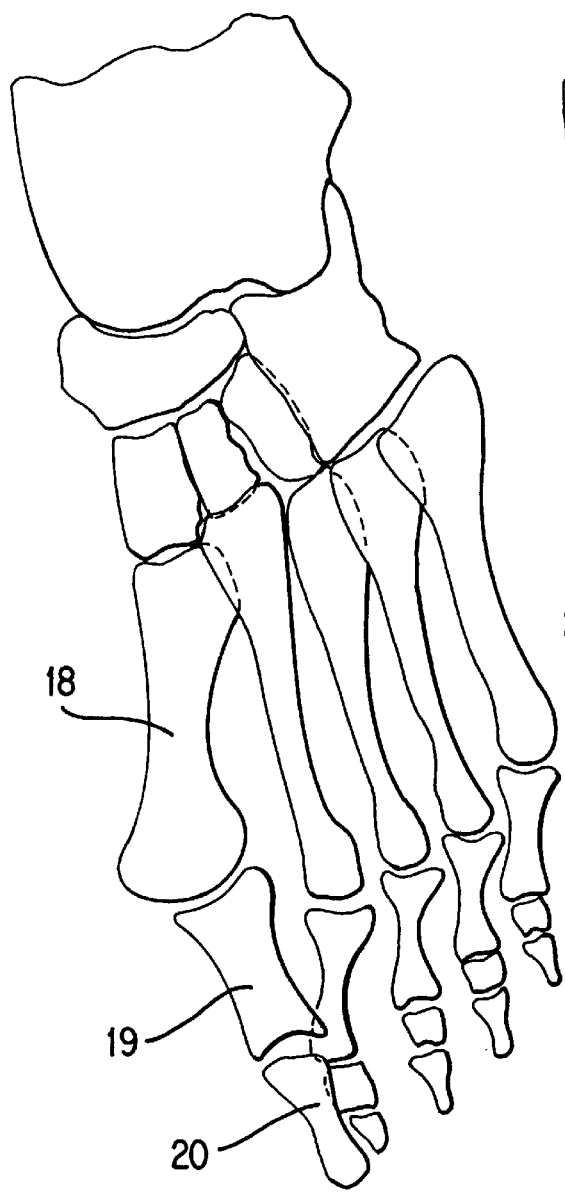
FIG. 1 is a top view of the bones of a foot subject to hallux valgus deformation.

FIG. 1 shows a foot suffering from hallux valgus deformation that is to be corrected: the hallux is formed by the first metatarsal 18, the first phalange 19 and the second phalange 20. The curvature of the hallux causes inward angular projection of the joint between the metatarsal and the phalange.

FIG. 2 shows the same foot after correction by the equipment of the invention: the first metatarsal 18 is corrected by the clip 21 shown in FIGS. 3 through 5 and the first phalange 19 is corrected by the clip 22 shown in FIG. 6.

The procedure is as follows:

in an intermediate area of the first metatarsal 18, using a bone saw, an exterior opening epiphysis-diaphysis osteotomy 23 avoiding the exterior cortical bone tissue makes an angular space in the bone at an angle equal to the required angular correction;

using the appropriate drilling guide, two parallel tunnels are bored into the spongy proximal part 24 of the epiphysis of the first metatarsal 18, at an angle B to the longitudinal axis of the metatarsal, the tunnels being positioned so that the angled joining area 4 of the clip 21 is substantially in line with the osteotomy 23;

the clip 21 is fitted by inserting the pins of the first anchor means 5 into the tunnels bored in the proximal part 24 of the first metatarsal 18, the body 1 of the clip 21 being bent first using the bending device to obtain the required correction as measured beforehand using an X-ray of the foot and/or during surgery using the protractor applied to the bone after osteotomy;

the clip 21 is immobilized temporarily by inserting a diaphysis pin 25 through the appropriate hole 12 as shown in FIGS. 3 through 5;

correct alignment of the bone in all planes is verified;

the clip 21 is fixed permanently by a bone screw 26 in the diaphysis of the first metatarsal 18;

the diaphysis pin 25 is either removed or can be left in place in the case of an unstable mounting.

If this correction of a hallux valgus deformation is insufficient, the first phalange 19 has also to be corrected by an interior closing osteotomy 27 of the diaphysis. The angle of the osteotomy is determined by a cutting guide and can be approximately 5°, approximately 10° or approximately 15°, for example.

The closure is stabilized by the clip 22 shown in FIG. 6, i.e. a clip with four pins of unequal length, two pins being inserted into each bone fragment to prevent any movement.

The clip 22 is fitted after predrilling the bone using appropriate ancillary equipment. The ancillary equipment and the clip 22 have an appropriate angular configuration to fit the shape of the diaphysis after closure of the osteotomy at the time of application.

The predrilling is carried out so that the clip when fitted has its angled joining area 4 substantially in line with the osteotomy 27.

Of course, the clip 22 can be used independently of a clip 21.

FIG. 2 also shows correction of rotation of the fifth metatarsal 28 by the clip 29 with one pin as shown in FIG. 5. After intermediate osteotomy 30 and correction by axial rotation of the two sections of the fifth metatarsal 28 relative to each other, the clip 29 is anchored by its single pin 6 in the first segment and fixed to the second segment by a bone screw 31.

The present invention is not limited to the embodiments explicitly described above, but includes variants and generalizations thereof within the scope of the following claims.

I claim:

1. Instrument for correcting deformation of small long bones in the human body comprising at least one bone holding device (21) including:

a rigid elongate body (1) having two rectilinear and entirely straight main segments (2, 3) joined together, the two main segments being joined together by an angled joining area at a first angle which can be varied so that it is substantially equal to a required angular correction to be applied to the bone, first anchor means (5) formed in one-piece with the first main segment (2) of the body (1) adapted to be fixed transversely into a bone, the first anchor means (5) including at least one pin (6, 7) extending in a direction substantially at a second angle (B) relative to the longitudinal axis of the first main segment (2) of the body (1), second anchor means (9) on the second main segment (3) of the body (1) adapted to be fixed transversely in the bone at a subsequent stage, after fixing of the first anchor means (5), wherein:

said first main segment (2) is directly connected to said first anchor means (5). and said second main segment (3) is directly connected to said second anchor means (9), and wherein said first and second main segments are directly connected to each other, said body (1) is made from a material and has a shape adapted to withstand without breaking and to retain permanent angular deformation in the angled joining area (4), the angled joining area has a thickness (E) substantially smaller than its width (L1), so that the equipment is adapted to be bent by means of a bending device to obtain the required correction and after an opening osteotomy (23) or a closing osteotomy (27) between two adjacent portions of small long bones at said first angle substantially equal to the required correction, the first anchor means (5) of the device can be anchored in the bone in a direction at said second angle (B) to the longitudinal axis of the bone, with the angled joining area (4) in line with the osteotomy (23, 27), and the device (21) determines a required angular offset between the two adjacent bone portions, subsequent anchoring of the second anchor means (9) fixing the angular offset.

2. Instrument according to claim 1 wherein:

the second anchor means (9) include at least one hole (10) adapted to fit a bone screw, the anchor means (5, 9) are adapted to penetrate the bone and project from a face (8) of the body (1) which face is opposite said first anchor means.

3. Instrument according to claim 2 wherein the body (1) includes near the hole (10) adapted to fit a bone screw a secondary hole (12) for a removable pin (25) for temporary fixing or strengthened fixing of the device (21) to the bone.

4. Instrument according to claim 1 wherein the angle (A) between the two main segments (2, 3) of the body (1) is equal to approximately 150.

5. Instrument according to claim 1 wherein the body (1) has a length (L2) between one third and one half the length of the bone which it is to correct.

6. Instrument according to claim 1 including it includes a drilling guide for boring penetration holes for the first anchor means (5) in a direction at a particular angle (B) to the longitudinal axis of the bone and a bending device adapted to shape the body (1) of the first bone holding device (21) to the required angle (A).

7. Instrument according to claim I including a complementary device having a rigid elongate body (100), the body having a convex side, the body comprising a rectilinear first main segment (2) and a rectilinear second main segment (3) joined together at an angled joining area (4) and wherein:

third anchor means (5) include a first pair of pins (13, 14) offset longitudinally on the body (100), fourth anchor means (9) include a second pair of pins (15, 16) offset longitudinally on the body (100), the pins (13–16) are parallel to each other and project from the convex side (17) of the body (100).

8. Instrument according to claim 7 wherein the pins (13, 14; 15, 16) of the same pair of anchor means are of different lengths, with an end pin (13, 16) longer than the intermediate pin (14, 15).

9. Instrument according to claim 7 wherein the angle between the two main segments (2, 3) of the body (100) is equal to approximately 100.

10. Method for correcting deformation of a small long bone in the human body, comprising the steps of:

providing a bone holding device including a rigid elongate body with two rectilinear main segments joined together. first anchor means on the first main segment of the body adapted to be fixed transversely into the bone, the first anchor means including at least one pin extending in a direction substantially at a particular angle relative to the longitudinal axis of the first main segment of the body, second anchor means on the second main segment of the body adapted to be fixed transversely in the bone, the two main segments being joined together by an angled joining area at an angle which is substantially equal to the required angular correction to be applied to the bone, said body being made from a material and having a shape adapted to withstand without breaking and to retain permanent angular deformation in the angled joining area, the angled joining area having a thickness substantially smaller than its width:

in an intermediate area of said small long bone, using a bone saw. providing an epiphysis-diaphysis osteotomy avoiding the exterior cortical bone tissue and making an angular space in the bone at an angle equal to the required angular correction.

using an appropriate drilling guide, boring two parallel tunnels into the spongy proximal part of the epiphysis of said small long bone, at said angle to the longitudinal axis of the bone, the tunnels being positioned so that the angled joining area of the bone holding device is substantially in line with the osteotomy;

inserting the pins of the first anchor means into the tunnels bored in the proximal part of said bone;

immobilizing temporarily said bone holding device by inserting a diaphysis pin through an appropriate hole:

verifying correct alignment of the bone in all planes; and permanently fixing the bone holding device by a bone screw in the bone.

11. The method of claim 10 further comprising the preliminary steps of:

measuring the required angular correction on the bone;

bending the bone holding device using a bending device at an angle substantially equal to the required correction.

12. Instrument for correcting deformation of small long bones in the human body comprising at least one bone holding device (21) including:

a rigid elongate body (1) having two rectilinear main segments (2, 3) joined together, the two main segments being joined together by an angled joining area at a first angle which can be varied so that it is substantially equal to a required angular correction to be applied to the bone, first anchor means (5) on the first main segment (2) of the body (1) adapted to be fixed transversely into a bone, the first anchor means (5) including at least one pin (6, 7) extending in a direction substantially at a second angle (B) relative to the longitudinal axis of the first main segment (2) of the body (1), second anchor means (9) on the second main segment (3) of the body (1) adapted to be fixed transversely in the bone at a subsequent stage, after fixing of the first anchor means (5), wherein:

said body (1) is made from a material and has a shape adapted to withstand without breaking and to retain permanent angular deformation in the angled joining area (4), the angled joining area has a thickness (E) substantially smaller than its width (L1), so that the equipment is adapted to be bent by means of a bending device to obtain the required correction and after an opening osteotomy (23) or a closing osteotomy (27) between two adjacent portions of small long bones at said first angle substantially equal to the required correction, the first anchor means (5) of the device can be anchored in the bone in a direction at said second angle (B) to the longitudinal axis of the bone, with the angled joining area (4) in line with the osteotomy (23, 27), and the device (21) determines a required angular offset between the two adjacent bone portions, subsequent anchoring of the second anchor means (9) fixing the angular offset, wherein the instrument includes a drilling guide for boring penetration holes for the first anchor means (5) in a direction at said second angle (B) to the longitudinal axis of the bone and a bending device adapted to shape the body (1) of the first bone holding device (21) to the required angle (A).

13. An instrument for correcting deformation of small long bones in the human body, the instrument comprising:

a rigid elongated body having first and second entirely straight main segments, the first and second main segments being directly connected, respectively, to first and second anchor means, the anchor means comprising means for attaching the body to a bone, the first main segment and the first anchor means being formed in one-piece, the first and second main segments also being directly connected to each other at an angle, wherein said angle of connection is controllably variable.

14. The instrument of claim 13, wherein the first anchor means is integrally formed with the body, and wherein the second anchor means is distinct from the body.

* * * * *

UNITED STATES PATENT AND TRADEMARK OFFICE
CERTIFICATE OF CORRECTION

PATENT NO.    : 5,810,822
DATED         : September 22, 1998
INVENTOR(S)   : Jean-Pierre Mortier It is certified that error appears in the above-identified patent and that said Letters Patent is hereby corrected as shown below:

| | |
|---|---|
| Title page Abstract, line 12 | delete "n" and insert --in-- |
| Col. 3, line 14 | delete "DRAWING" and insert --DRAWINGS-- |
| Col. 7, line 63 | delete "150" and insert --15°-- |
| Col. 8, line 1 | delete "it includes" |
| Col. 8, line 7 | delete "I" and insert --1-- |
| Col. 8, line 24 | delete "100" and insert --10°-- |
| Col. 8, line 44 | delete ":" and insert --;-- |
| Col. 8, line 46 | delete "." and insert --,-- |
| Col. 8, line 49 | delete "." and insert --;-- |
| Col. 8, line 59 | delete ":" and insert --;-- |

Signed and Sealed this

Twenty-third Day of March, 1999

Attest:

Q. TODD DICKINSON

Attesting Officer

Acting Commissioner of Patents and Trademarks